United States Patent
Muhar

(10) Patent No.: US 6,254,294 B1
(45) Date of Patent: Jul. 3, 2001

(54) PHARMACEUTICAL KIT

(76) Inventor: Sigrid G. Muhar, 3 Sea La. S., St. Petersburg, FL (US) 33705

(*) Notice: Subject to any disclaimer, the term of this patent is extended or adjusted under 35 U.S.C. 154(b) by 0 days.

(21) Appl. No.: 09/632,436

(22) Filed: Aug. 4, 2000

Related U.S. Application Data

(60) Provisional application No. 60/147,972, filed on Aug. 9, 1999, and provisional application No. 60/187,768, filed on Mar. 8, 2000.

(51) Int. Cl.[7] .............................. A61J 1/00; B05B 11/00; B65D 69/00
(52) U.S. Cl. .......................... 401/26; 206/572; 401/119; 401/124; 401/125; 401/195; 401/203; 401/207; 604/2
(58) Field of Search .................... 401/17, 23, 26, 401/34, 119, 123, 124, 125, 195, 203, 207; 206/209, 570, 571, 572; 604/2

(56) References Cited

U.S. PATENT DOCUMENTS

| | | | |
|---|---|---|---|
| 3,938,898 | * 2/1976 | Reitknecht | 401/207 X |
| 4,685,907 | * 8/1987 | Agren et al. | 424/447 |
| 4,686,211 | * 8/1987 | Hara et al. | 514/148 |
| 5,503,847 | * 4/1996 | Queen et al. | 424/488 |
| 5,614,583 | * 3/1997 | Tseng et al. | 524/555 |
| 5,779,053 | * 7/1998 | Partika et al. | 206/570 |
| 5,848,700 | * 12/1998 | Horn | 206/570 |
| 5,850,630 | * 12/1998 | Wilson | 704/270 |
| 5,885,237 | * 3/1999 | Kadash et al. | 602/48 |
| 5,979,658 | * 11/1999 | Allen et al. | 206/572 |
| 6,116,426 | * 9/2000 | Slonim | 206/570 |
| 6,206,192 | * 3/2001 | Winstead et al. | 206/572 |

FOREIGN PATENT DOCUMENTS

2114614 * 7/1998 (RU).

* cited by examiner

Primary Examiner—Gregory L. Huson
Assistant Examiner—Kathleen J. Prunner

(57) ABSTRACT

A pharmaceutical kit includes a container; a packet of dispensing swabs; a bottle with a dispenser assembly with an upwardly extending tubular member with an open aperture at the top for the passage of fluid from the bottle through the dispenser assembly, the tubular member adapted to removably receive a short tube of a dispensing swab; a quantity of liquid iodine located within the bottle; and a tube containing a quantity of zinc oxide.

1 Claim, 3 Drawing Sheets

PHARMACEUTICAL KIT

RELATED APPLICATION

This is a continuation in part application of co-pending Provisional Application No. 60/147,972 filed Aug. 9, 1999 entitled "Disposable Cotton Swab Applicator Tip" and Provisional Application No. 60/187,768 filed Mar. 8, 2000 entitled "Methods of Treatment and Composition of Preparations for the Herpes Simplex Virus Type I and II."

BACKGROUND OF THE INVENTION

1. Field of the Invention

The present invention relates to a pharmaceutical kit and more particularly pertains to providing a complete regimen of medications and components necessary for the treatment of a skin malady.

2. Description of the Prior Art

The use of pharmaceutical and medical kits of known designs and configurations is known in the prior art. More specifically, pharmaceutical and medical kits of known designs and configurations previously devised and utilized for the purpose of treating maladies through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,927,884 to Kao relates to a disposable perfume stick.

While various known devices and methods fulfill their respective, particular objectives and requirements, the existing patents do not describe a pharmaceutical kit that allows providing a complete regimen of medications and components necessary for the treatment of a skin malady.

In this respect, the pharmaceutical kit according to the present invention substantially departs from the conventional concepts and designs of the prior art, and in doing so provides an apparatus primarily developed for the purpose of providing a complete regimen of medications and components necessary for the treatment of a skin malady.

Therefore, it can be appreciated that there exists a continuing need for a new and improved pharmaceutical kit which can be used for providing a complete regimen of medications and components necessary for the treatment of a skin malady. In this regard, the present invention substantially fulfills this need.

SUMMARY OF THE INVENTION

In view of the foregoing disadvantages inherent in the known types of pharmaceutical and medical kits of known designs and configurations now present in the prior art, the present invention provides an improved pharmaceutical kit. As such, the general purpose of the present invention, which will be described subsequently in greater detail, is to provide a new and improved pharmaceutical kit and method which has all the advantages of the prior art and none of the disadvantages.

To attain this, the present invention essentially comprises a pharmaceutical kit providing a complete regimen of medications and components necessary for the treatment of a skin malady. First provided is a container formed in a rectilinear configuration. The container has a closed bottom and an open top. The container also has a sidewall between the bottom and the top. The container also has a removable lid selectively positionable over the open top. Next provided is a packet of dispensing swabs contained within the container. Each swab includes an essentially rigid short tube. The tube has a lower opening and an upper opening. The tube has a quantity of cotton secured over the upper opening. In operation and use, liquid medication passes through the tube to the swab and then to the malady to be treated. Next provided is a bottle. The bottle has a closed bottom and an open top. The bottle also has a sidewall between the bottom and top. Female screw threads of a first diameter are provided around the open top. The bottle also has a dispenser assembly. The dispenser assembly has a lower end. Male screw threads are provided around the lower end of the dispenser assembly. The male screw threads are adapted to removably couple with respect to the female screw threads of the bottle for bottle refilling purposes. The dispenser assembly has an upwardly extending tubular member. An open aperture is provided at the top of the upwardly extending tubular member for the passage of fluid from the bottle through the dispenser assembly. The tubular member is adapted to removably receive a short tube of a dispensing swab during operation and use. A tubular sleeve is provided. The tubular sleeve has a closed top positionable over the tubular member during storage. Next provided is a cap. The cap is in a generally cylindrical configuration and is adapted to be removably positioned over the dispenser assembly during storage and to be removed during operation and use. Next provided is a quantity of liquid iodine. The liquid iodine is located within the bottle to be dispensed through the dispenser assembly and dispensing swab during inversion. A tube is next provided. The tube has a closed bottom and an open top. The tube also has a squeezable sidewall between the bottom and the top. Male screw threads are provided around the open top. An associated cover has internal female screw threads adapted to be removably received over the screw threads adjacent to the open top. Next provided is a quantity of zinc oxide. The zinc oxide is located within the tube. The zinc oxide is adapted to be dispensed upon squeezing the sidewall of the tube. In this manner prior to the application of the zinc oxide, the iodine is applied to the area of the user. Finally, a set of instructions for the utilization of the iodine and the zinc oxide is provided.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved pharmaceutical kit which has all of the advantages of the prior art pharmaceutical and medical kits of known designs and configurations and none of the disadvantages.

It is another object of the present invention to provide a new and improved pharmaceutical kit which may be easily and efficiently manufactured and marketed.

It is further object of the present invention to provide a new and improved pharmaceutical kit which is of durable and reliable construction.

An even further object of the present invention is to provide a new and improved pharmaceutical kit which is susceptible of a low cost of manufacture with regard to both materials and labor, and which accordingly is then susceptible of low prices of sale to the consuming public, thereby making such pharmaceutical kit economically available to the buying public.

Even still another object of the present invention is to provide a pharmaceutical kit for providing a complete regimen of medications and components necessary for the treatment of a skin malady.

Lastly, it is an object of the present invention to provide a new and improved pharmaceutical kit including a container; a packet of dispensing swabs; a bottle with a dispenser assembly with an upwardly extending tubular member with an open aperture at the top for the passage of fluid from the bottle through the dispenser assembly, the tubular member adapted to removably receive a short tube of a dispensing swab; a quantity of liquid iodine located within the bottle; and a tube containing a quantity of zinc oxide.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
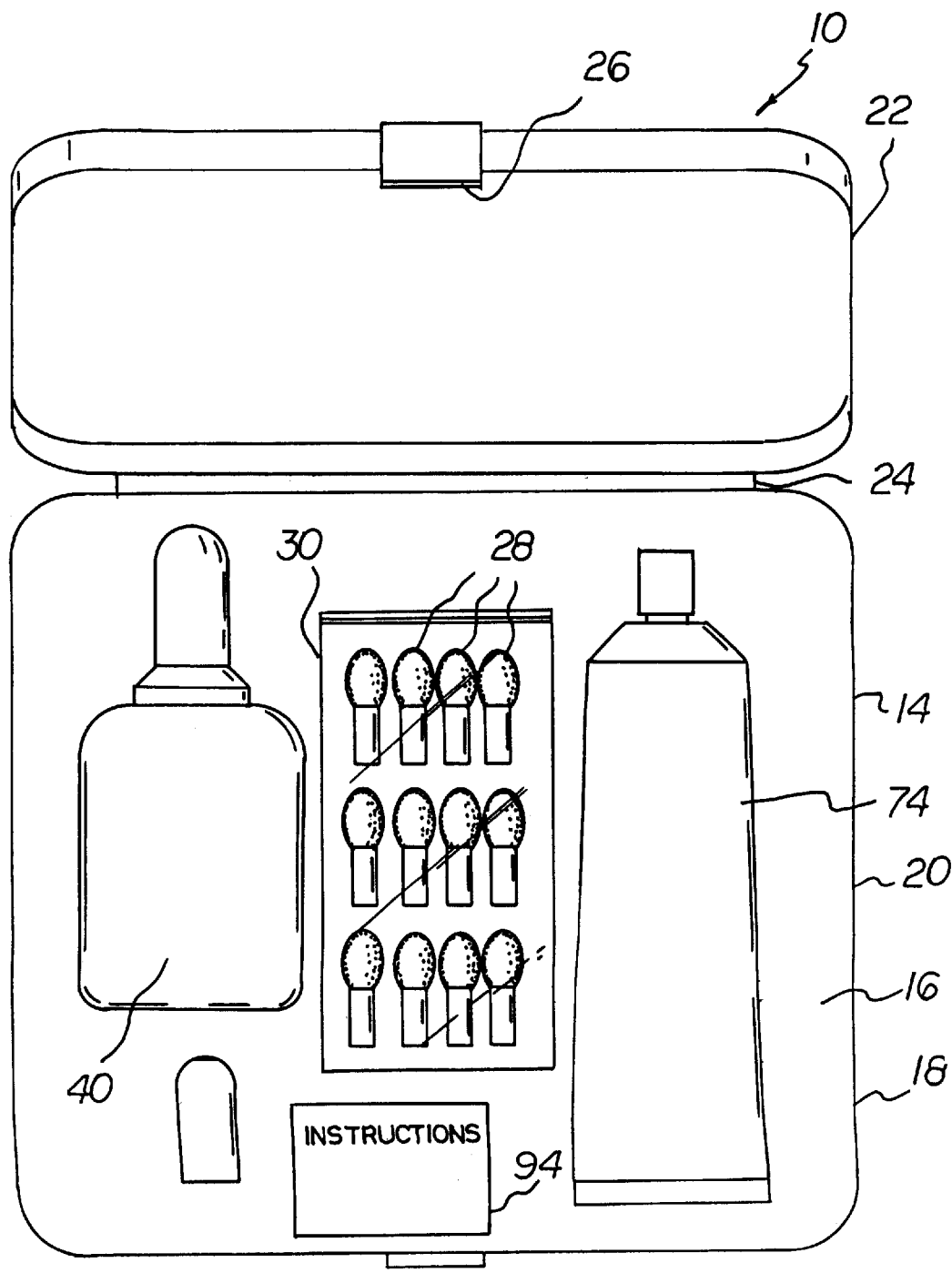
FIG. 1 is a perspective illustration of the new and improved pharmaceutical kit constructed in accordance with the principles of the present invention.
Figure 2:
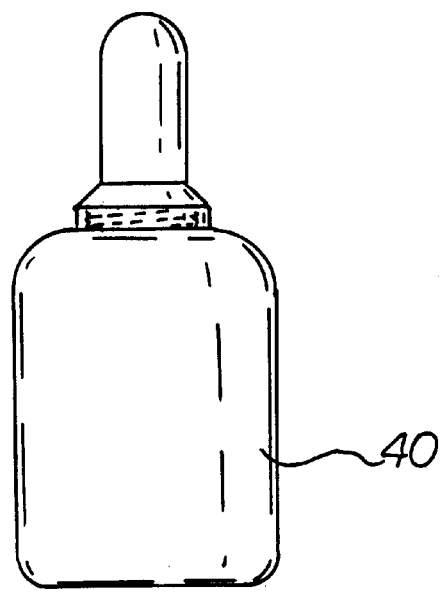
FIG. 2 is a front elevational view of the bottle shown in FIG. 1.
Figure 5:
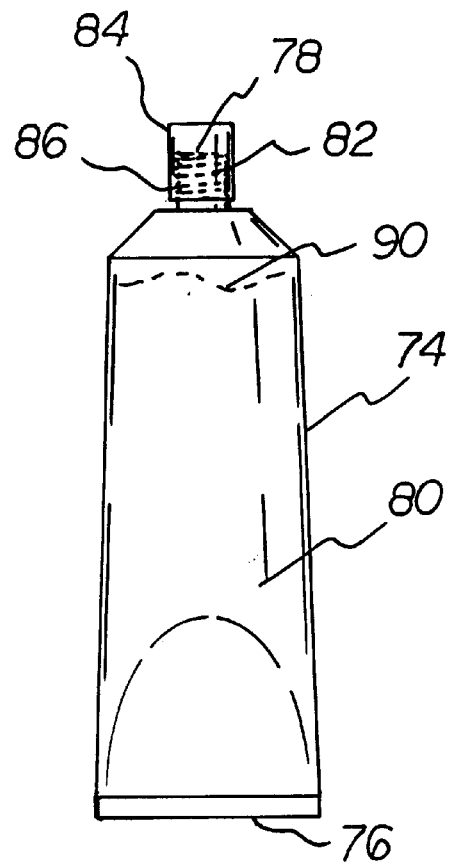
FIG. 5 is a front elevational view of the tube shown in FIG. 1.
Figure 3:
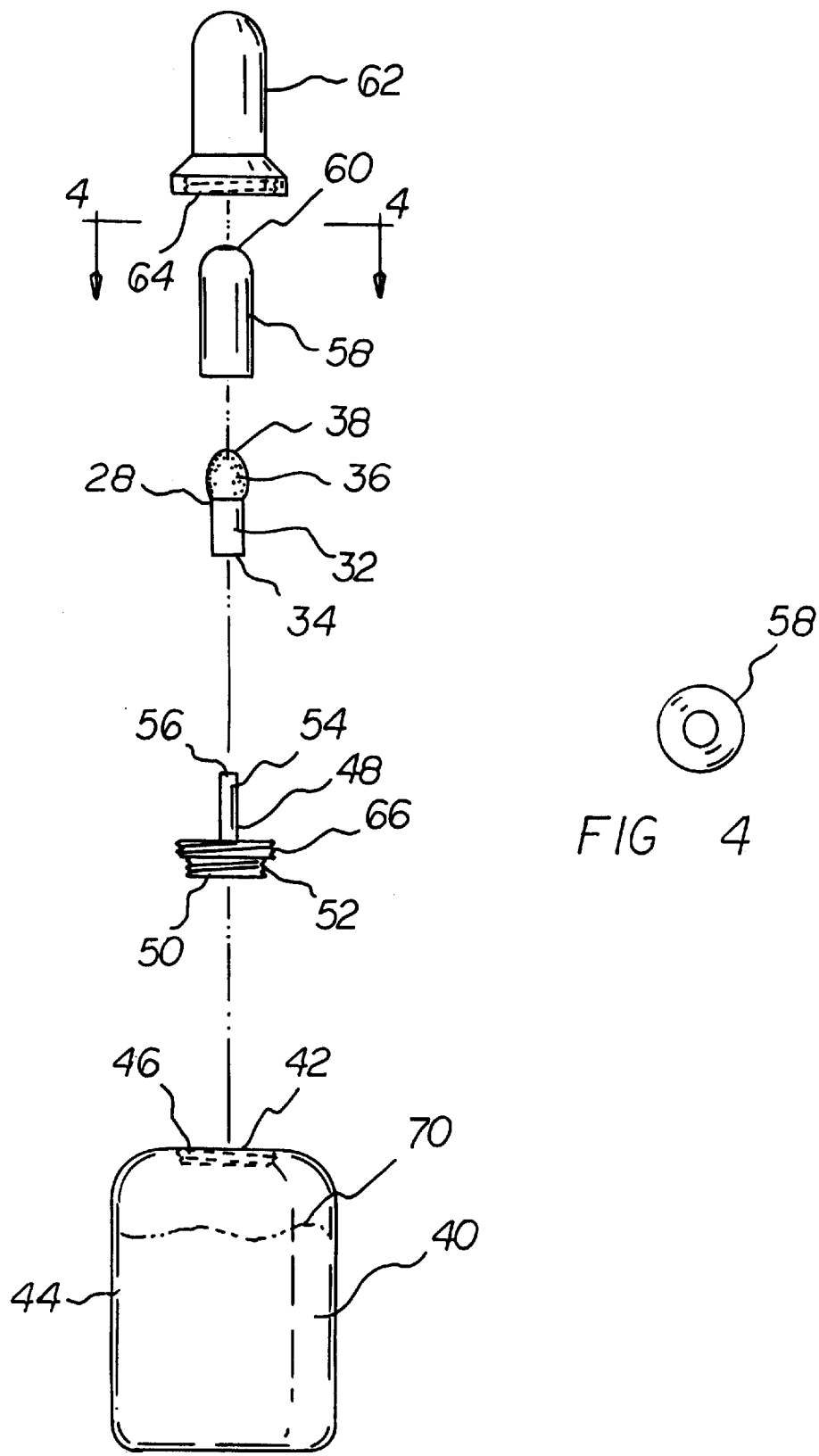
FIG. 3 is an exploded view of the bottle as shown in FIGS. 1 and 2.
Figure 4:
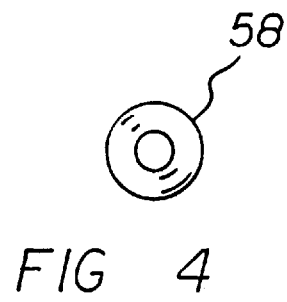
FIG. 4 is a cross-sectional view taken along line 4—4 of FIG. 3.

With reference now to the drawings, and in particular to FIG. 1 thereof, the preferred embodiment of the new and improved pharmaceutical kit embodying the principles and concepts of the present invention and generally designated by the reference numeral 10 will be described.

The present invention, the pharmaceutical kit 10 is comprised of a plurality of components. Such components in their broadest context include a container, a packet of dispensing swabs, a bottle, a quantity of liquid iodine, a tube, and a quantity of zinc oxide. Such components are individually configured and correlated with respect to each other so as to attain the desired objective.

A pharmaceutical kit 10 for providing a complete regimen of medications and components necessary for the treatment of a skin malady includes a container 14 formed in a rectilinear configuration. The container has a closed bottom 16 and an open top 18. The container also has a sidewall 20 between the bottom and the top. The container also has a removable lid 22 selectively positionable over the open top and preferably coupled thereto by a living hinge 24 with a clasp 26.

Next provided is a packet of dispensing swabs 28 contained within the container such as in a resealable envelope 30. Each swab includes an essentially rigid short tube 32. The tube has a lower opening 34 and an upper opening 36. The tube has a quantity of cotton 38 secured over the upper opening. In operation and use, liquid medication passes through the tube to the swab and then to the malady to be treated.

Next provided is a bottle 40. The bottle has a closed bottom and a top with an opening 42. The bottle also has a sidewall 44 between the bottom and top. Female screw threads 46 of a first diameter are provided around the open top. The bottle also has a dispenser assembly 48. The dispenser assembly has a lower end 50. Male screw threads 52 are provided around the lower end of the dispenser assembly. The male screw threads are adapted to removably couple with respect to the female screw threads of the bottle for bottle refilling purposes. The dispenser assembly has an upwardly extending tubular member 54. An open aperture 56 is provided at the top of the upwardly extending tubular member for the passage of fluid from the bottle through the dispenser assembly. The tubular member is adapted to removably receive the short tube of a dispensing swab during operation and use. A stopper formed as a tubular sleeve 58 is provided. The tubular sleeve has a closed top 60 positionable over the tubular member during storage.

Next provided is a cap 62. The cap is formed in a generally cylindrical configuration with female threads 64 at the bottom. It is adapted to be removably positioned over male threads 66 of the dispenser assembly during storage. The cap is adapted to be removed during operation and use.

Next provided is a quantity of liquid iodine 70. The liquid iodine is located within the bottle to be dispensed through the dispenser assembly and dispensing swab during inversion.

A tube 74 is next provided. The tube has a closed bottom 76 and an open top 78. The tube also has a squeezable sidewall 80 between the bottom and the top. Male screw threads 82 are provided around the open top. An associated cover 84 has internal female screw threads 86. The cover is adapted to be removably received over the screw threads adjacent to the open top.

Next provided is a quantity of zinc oxide 90. The zinc oxide is located within the tube. The zinc oxide is adapted to be dispensed upon squeezing the sidewall of the tube. In this manner prior to the application of the zinc oxide, the iodine is applied to the area of the user.

Finally, a set 94 of instructions for the utilization of the iodine and the zinc oxide is provided.

The present invention is a sequential skin application of three therapeutic agents, known by the prior art, for the treatment of viral infection caused by herpes simplex I, presenting as sores on lips known as cold sores or fever blisters, and herpes simplex II, presenting as genital sores. Two of the compounds will be combined in one product to enhance their therapeutic effectiveness. The combined treatment will promote the alleviation of secondary bacterial infection occurring in these sores, presenting as very painful and swollen disfigurements. Additionally, this invention utilizes packaging and instruction for use of the preparations for the purpose of first eliminating the virus and then healing the sores. A properly labeled box containing the therapeutic agents will benefit the consumer by, 1. alerting the consumer to this treatment choice, 2. promoting prompt treatment at onset of symptoms, reducing pain and suffering, 3. securing virtually no medication side affects, 4. minimizing the use of oral antibiotics, treatment of secondary bacterial infection, and 5. reducing health care cost.

Community pharmacists are repeatedly challenged by customers, suffering from the skin eruptions of herpes virus, in finding an effective and practical treatment. One solution is recommending two commercially available agents Povidone Iodine and Zinc oxide pastes or ointments to be applied sequentially. This treatment modality is not generally known but has been proved "very effective" in practical experience.

The search for a useful compound for the prophylaxis and treatment of viral infection in general has been very difficult because in contrast to most other infectious agents, viruses utilize active metabolic participation of the invaded cell. Thus any compounds capable of eradicating the virus may also injure the invaded cell. Additionally, by the time symptoms of the infection manifest themselves, the virus has done its damage and prophylaxis is useless. But alleviating the pain and suffering of the expression of oral or genital sores can still be minimized by using a variety of known products.

Historically, more or less successful treatment ideas and modalities were utilized, where risks of side-effects outweigh the benefits of the treatments. Treatments include smallpox vaccinations, fluorescent light on petrotricyclic dyes, chloroform and ether, certain Bacilli, Levamisole (anthelmintic), idoxuridine, vidarabine, trifluridine, in addition to the newer oral agents as acyclovir, valacyclovir.

There is no known method of treatment in the prior art of using three therapeutic agents, two of which are combined in one, placed in a kit designed to instruct the consumer to sequentially use these ingredients. Inasmuch as these three compounds have been used in the past for a variety of skin ailments, a treatment kit is necessary to raise the awareness of a treatment choice that is not obvious to the consumer. The compounds are the antimicrobial iodine, the healing and soothing agent zinc oxide, and the mildly anti-infective oxyquinolone sulfate.

Iodine is an antimicrobial, a halogen containing compound. In its elemental form, it is known to be lethal to microflora, microzoa and to viruses. Iodine has been used as a skin disinfectant since 1839 and has remained in use because of its efficacy, low toxicity, and economy. Several different forms and strengths of iodine are utilized, such as the sodium salt (NaI), potassium salt (KI), e.g. Iodine Tincture, Strong Iodine Solution (Lugol's Solution), and Iodine Solution, combining strength from 2% NaI to 10% KI. Although the tinctures and solutions releasing the I3-ion are very effective, their tendency to cause stinging and burning of the skin discourage use. Another way to deliver the free iodine (I2) to the skin is through the use of the iodophor complex [polyvinylpyrrolidone (PVP)]. A presently widely used PVPI complex is Povidone Iodine (BETADINE).

Zinc is a mildly antibacterial and healing agent. As an essential element, zinc is ubiquitous in almost all living cells. Zinc is tightly regulated in the human body and toxicities are rare. Toxicities of zinc are described far less often in the medical literature than are zinc deficiencies. A confirmation of the safety of external applications of water insoluble zinc compounds is evident by its widespread and historical use as a protectant, astringent, healing, and mild disinfecting agent.

Zinc oxide as a paste is the good choice in this preparation for two reasons. A greater percentage of zinc is possible in the paste; this is necessary to liberate sufficient zinc ion for protein precipitation of viral and secondary bacterial and other microorganisms in addition to healing; and the paste will contribute greater adherence to the skin.

Oxyquinolone sulfate is a mild bacteriostatic and fungistatic. This compound is added to the zinc oxide paste for two reasons: first to increase water miscibility by the formation of zinc sulfate (an astringent and mild antiseptic in its own right) in the mixture, and secondly to increase the microbiostatic property of the paste.

Finding a means to create public awareness of the availability and proper usage of three already known compounds to treat viral skin damage is the main purpose of this invention. The components of the kit are described herein above and herein below.

Povidone iodine (PVPI) solution must be dispensed in a convenient plastic applicator vial with an attached disposable cotton swab applicator tip. A PVPI 10% solution is the preferred compound in this kit; it is just as effective a the tincture or solution but much less irritating.

Zinc oxide/oxyquinolone sulfate paste is preferred over the ointment for three reasons: 1. a greater percentage of zinc is possible, more zinc ions are available for treatment; 2. more zinc ions will be liberated when prepared with white petrolatum or beeswax, water miscibility is increased and zinc oleate or zinc stearate formation is reduced; and 3. a greater adherence to the skin is promoted by the paste.

In preparing the zinc oxide/oxyquinolone sulfate paste the following steps are necessary. To achieve the desired percentage, 400 g of zinc oxide and 0.15 g of oxyquinolone sulfate must be levigated with enough glycerin or mineral oil to moisten the powders. This will facilitate incorporation into a mixture of 100 g of starch, or other inert binder and 500 g of white petrolatum or beeswax for a total of 1000 g. Beeswax is currently thought to be the preferred vehicle. A possible vehicle variation could be 250 g of white petrolatum and 250 g of beeswax.

The preferred contents of the kit for at least 30 applications are:

1. Povidone Iodine in a 30 ml bottle;
2. Zinc oxide/oxyquinolone 40%/0.15% paste in a 30 gram tube;
3. 30 disposable cotton tips contained in a clear plastic bag; and
4. Instructions for use.

Liquid medicines are often dispensed in bottles which deliver drops orally or to the affected area of eyes, ears, or various areas of skin. For therapeutic solutions to be applied to the skin that necessitates a contact of about 30 to 60 seconds, and a non-contaminated medium, there is a need for disposable cotton swab applicators tips, which can be mounted directly to the dispenser of the treatment fluid.

The applicators presently in use are non-disposable applicators for reuse of liquids to large areas; these may be adequate for healthy skin only. One disposable cotton tip patented in Jul. 27, 1999, U.S. Pat. No. 5,927,884 is related but sufficiently different because it lacks the utility which necessitates the present invention.

The main objectives of the disposable cotton swab applicator tips are the ease of application of liquid medicine and other liquids, and ensuring adequate amounts of medicine to be flowing to the cotton tip while in contact with the affected skin, and to impede back flow of liquid into the dispenser. Another objective is a reduction of recontaminating of both the affected area of skin and the remaining liquid medicine in the bottle. Further objectives are the discouragement of using bare fingers or hands to apply medicines in order to prevent introducing micro-organisms to the affected area of skin and to prevent absorbing of harmful medicines in fingers or hands when not needed. Finally, a related objective is the reduction of waste by using the cotton swab tip versus soaking up cotton balls or slapping on medicines or other liquids with bare fingers or hands.

The principle objective of the present invention is the easy delivery of liquid medicines or other liquids to the affected area of skin by means of non-contaminated disposable cotton swab applicator tips. Additional objectives are insuring adequate flow and sufficient contact of liquid medicines or other liquids with the affected skin while preventing back flow of contaminated liquid into the dispenser. Further objectives are the preventing of recontaminating of both the skin area treated and the treatment liquid by using a cotton swab applicator tip instead of bare fingers or hands.

To realize these and other objectives of the present invention there is a plastic dispensing container of conventional known material with a narrow tip and a small opening. A disposable tube with a slightly larger opening and being just wide enough to fit firmly over the tip of the applicator bottle must be half covered with once sterilized cotton fibers. The need for final sterility of the cotton swab tip depends on the purpose and type of liquid intended. Using precise measurements, shapes, and materials in the design of the preferred embodiments will benefit from natural forces such as pressure, capillary action, and osmotic pressure to aid in a formulation of a simple but practical product.

It will be appreciated that various other measurements, as discussed below, are possible without departing from the spirit of the relationship of the dimensions. The measurements applied below are for ease of comparisons only as will be demonstrated.

The objective of securing the disposable cotton swab tip while in use is met by friction and pressure.

(1) Friction is provided by the sufficiently long tubes both the length of the tip of the dispensing bottle and the disposable cotton tip.

(2) Again, friction and inward pressure is provided by the tube of the disposable cotton tip that has a diameter just large enough for easy yet secure fit.

(3) Pressure to the disposable cotton tip is accomplished simply when the product is ultimately utilized.

The objective of preventing back flow of medicine or other liquids, into the dispensing bottle, to avoid contamination, is achieved by using the right material and by varying the shapes and dimensions of the preferred embodiments.

(4) Using a porous material like cardboard or a mixture of the group of cardboard or plastics, as the base of the disposable cotton tip, is one way to prevent back flow of medicine into the dispensing bottle; cardboard absorbs by capillary action. Biodegradability is a side benefit of using cardboard instead of material of the group of plastics.

(5) A further reduction of back flow is accomplished by the larger size of the circular opening at the top of the dome-shaped disposable cotton tip compared to the opening of the dispensing bottle. An additional benefit is a greater capillary flow into the cotton fiber through the larger opening.

(6) A sufficient length difference between the disposable cotton tip and the tip of the dispensing bottle, the former being about $1/16$ inch larger than the latter ensures no touching of the two tips and thus reduces back flow. Also, the small reservoir that has formed will aid to saturate the cotton fiber by capillary action, without risking any measurable waste of the liquid. In addition, any minute, if any, back flow will not be contaminated because micro-organisms would have to travel against osmotic pressure and capillary action.

(7) An upper-most dome-shaped top of both the tip of the dispensing bottle and the tip of the disposable cotton tip is the preferred shape. This shape will increase surface tension, and thus impede molecular flow back into the dispensing container.

(8) Placing the disposable cotton tip over instead of inserting it into the tip of the dispensing bottle will also diminish back flow.

The liquid dispensing bottle can be made of the group of plastics or glass known in prior art. The tube is about $15/16$ inch long and about $3/16$ inch in diameter. It has a circular opening of about $3/32$ inch at the upper-most dome-shaped end of the tube where liquid medicine exits. This opening will have a thin seal, aluminum foil or other, during storage to be pierced open when ready for use.

The tube of the disposable cotton tip is made of the group of plastics or cardboard, where cardboard is the preferred material. It is mounted over the applicator bottle tip when ready for use and is about $1/4$ inch in diameter. It consists of a hollow tube with an opening on the bottom and an about $1/8$ inch circular opening at the dome-shaped top. A dome-shape is preferred. The length of the disposable cotton tip tube is about 1 inch.

The cotton fiber used should be once sterilized, but may not remain sterile depending on the type of fluid used. The closure tip must have a tight fit at the top and sides; it should not form a reservoir such as occurs when the cotton tip is mounted. Instead the closure should have a small inward protrusion just the size of the opening of the dispensing bottle tip. The protrusion acts as a stopper that prevents leakage when not in upright position. Although the lid could function without the stopper, a stopper mechanism is preferred.

The method of treating a wound comprises the steps of applying iodine to a wound to be treated; mixing a mixture including zinc oxide and oxyguinolone; and applying the mixture to the wound. Alternatively, zinc oxide comprises about 40 percent of the mixture. In still another alternate method, the oxyguinolone comprises about 0.15 percent of the mixture.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pharmaceutical kit for providing a complete regimen of medications and components necessary for the treatment of a skin malady comprising, in combination:

a container formed in a rectilinear configuration with a closed bottom and an open top and a sidewall there between and a removable lid selectively positionable over the open top;

a packet of dispensing swabs contained within the container, each dispenser swab including an essentially rigid short tube with a lower opening and an upper opening and a quantity of cotton secured over the upper opening for the passage of liquid medication there through to the swab and then the malady to be treated;

a bottle with a closed bottom and an open top and a sidewall there between, the open top having female screw threads of a first diameter there around, the bottle also having a dispenser assembly with a lower end having male screw threads there around adapted to removably couple with respect to the female screw threads of the bottle for bottle refilling purposes, the dispenser assembly having an upwardly extending tubular member with an open aperture at the top for the passage of fluid from the bottle through the dispenser assembly, the tubular member adapted to removably receive the short tube of one of the dispensing swab during operation and use and a tubular sleeve with a closed top positionable over the tubular member during storage;

a cap in a generally cylindrical configuration adapted to be removably positioned over the dispenser assembly during storage and to be removed during operation and use;

a quantity of liquid iodine located within the bottle to be dispensed through the dispenser assembly and a respective dispensing swab during inversion;

a tube having a closed bottom and an open top with a squeezable sidewall therebetween, the open top having male screw threads there around with an associated cover with internal female screw threads adapted to be removably received over the male screw threads adjacent to the open top;

a quantity of zinc oxide located within the tube adapted to be dispensed upon squeezing the sidewall for application to the area of the user to be treated prior to the application of the iodine; and a set of instructions for the utilization of the iodine and the zinc oxide.

* * * * *